Figure 1:
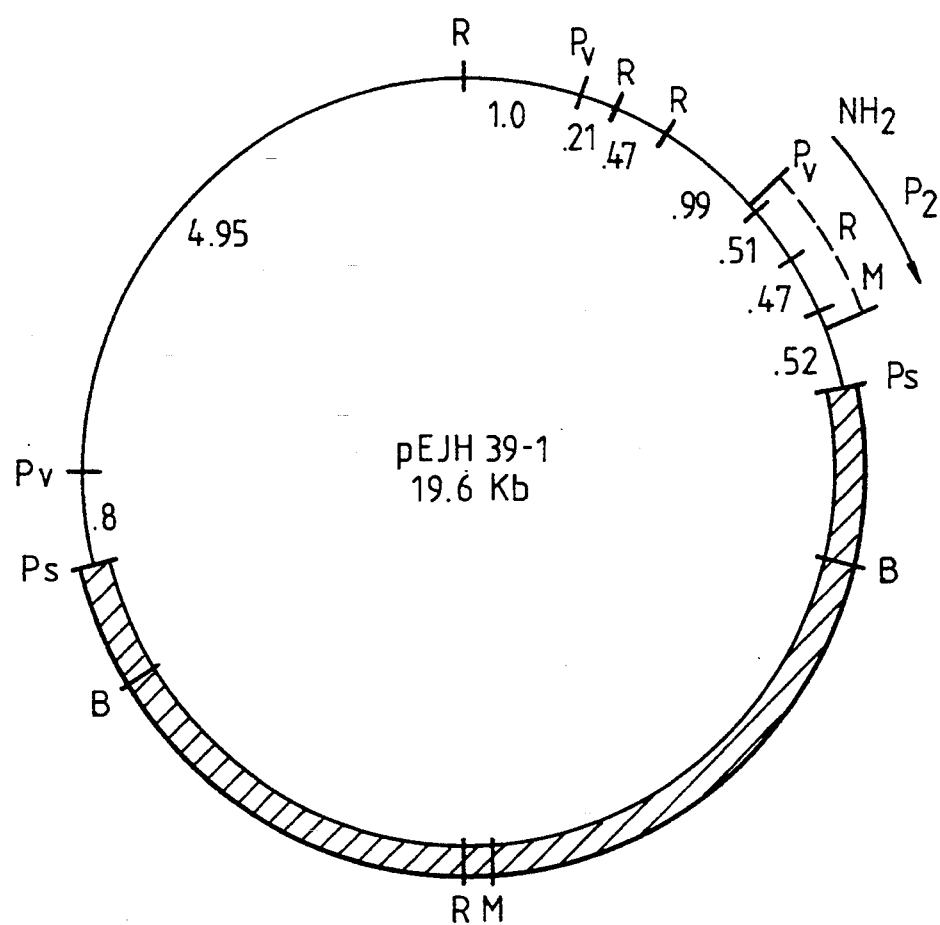

United States Patent [19]

Hansen

[11] Patent Number: 5,380,655
[45] Date of Patent: Jan. 10, 1995

[54] **METHODS AND COMPOSITIONS FOR THE PRODUCTION OF *HAEMOPHILUS INFLUENZAE* TYPE B MAJOR OUTER MEMBRANE PROTEIN ANTIGENS**

[75] Inventor: Eric J. Hansen, Plano, Tex.

[73] Assignee: Board of Regents, The University of Texas System, Austin, Tex.

[21] Appl. No.: 835,092

[22] Filed: Feb. 11, 1992

Related U.S. Application Data

[63] Continuation of Ser. No. 249,482, Sep. 23, 1988, abandoned, which is a continuation-in-part of Ser. No. 131,143, Dec. 10, 1987, abandoned.

[51] Int. Cl.[6] .................. C12N 1/21; C12N 15/31
[52] U.S. Cl. .................. 435/172.3; 435/252.3; 435/320.1; 536/23.7; 424/256.1
[58] Field of Search ............. 435/172.3, 320.1, 252.3, 435/69.3, 6; 530/324, 325, 326, 327, 328; 935/9, 11, 12, 29, 72

[56] References Cited

U.S. PATENT DOCUMENTS 4,554,101 11/1985 Hopp .................................. 514/2 X

FOREIGN PATENT DOCUMENTS 0133671 3/1985 European Pat. Off. ....... C12Q 1/68
WO88/04932 7/1988 WIPO .................... A61K 35/66

OTHER PUBLICATIONS

Gulig, P. A. et al. 1983. Infect. Immun. vol. 42 pp. 516–524
Benjamin, R. C., et al. 1984, *Gene* vol. 31 pp. 173–185.
Bulawa, C. E., et al. 1986. *Cell* vol. 46 pp. 213–225.
Mason, P. J., et al. 1985. "Hybridisation in the Analysis of Recombinant DNA" In *Nucleic Acid Hybridisation*, Ed. B. D. Hames et al., IRL Press, Oxford. pp. 113–137.
Munson, R. S., et al. 1983. *J. Clin. Invest.* vol. 72 pp. 677–684.
Watson, M. E. E. 1984. *Nucleic Acis Research* vol. 12 pp. 5145–5164.
EPO Search Report for EPC Application 88311691.5.
Danner et al. (1982), Gene, 18:101–105.
Thomas et al. (1986), *Infect. Immun.*, 52:812–817.
Loeb, M. R. (1987), Infect. Immun., 55:2612–2618.
Green et al. (1987), *Infect. Immun.*, 55:2878–2883.
Gonzales et al. (1987), *Abst. Ann. Meet. Am. Soc. Microbiol.*, 87:79.
Gonzales et al. (1987), *Infect Immun.*, 55:2993–3000.
Hansen et al. (1988), *Abs. Ann. Meet.*,–1988, Abs. No. D–172, p. 99.
Munson, R. S. (1988), *Abs. Ann. Meet.*,–1988, Abs. No. D–201, p. 104.
Munson et al. (1988), *Abs. 1988 ICAAC*, Abs. No. 1124, p. 308.
Munson et al. (1988), *Abs. 1988 ICAAC*, Abs. No. 1125, p. 308.
Munson et al. (1988), *Infect. Immun.*, 56:2235–2242.
Hansen et al. (1988), *Infect. Immun.*, 56:2709–2716.
Munson et al. (1989), *Infect. Immun.*, 57:88–94.
Hansen et al. (1989), *Infect. Immun.*, 57:1100–1107.

*Primary Examiner*—Richard A. Schwartz
*Assistant Examiner*—James Ketter
*Attorney, Agent, or Firm*—Arnold, White & Durkee

[57] ABSTRACT

Disclosed are DNA and other biological compositions, including biological cultures, for preparing *Haemophilus influenzae* antigens by recombinant means. The disclosed recombinant antigens are suitable for use in the preparation of immunogenic compositions for use in vaccination against various *Haemophilus influenzae* type B infections. Particular embodiments disclosed include DNA segments which encode the P2 major outer membrane protein antigen, also referred to as the 39/38 protein, biological cultures transformed by these DNA segments, and the preparation of recombinant P2 antigen through the use of these biological cultures.

26 Claims, 3 Drawing Sheets

METHODS AND COMPOSITIONS FOR THE PRODUCTION OF *HAEMOPHILUS INFLUENZAE* TYPE B MAJOR OUTER MEMBRANE PROTEIN ANTIGENS

The government may own certain rights in the present invention pursuant to NIH grant 4117671.

This application is a continuation of application Ser. No. 07/249,482, filed Sep. 23, 1988, now abandoned, which was a continuation-in-part of application Ser. No. 07/131,143, filed Dec. 10, 1987, now abandoned.

BACKGROUND OF THE INVENTION

1. Field of the Invention

The present invention relates to compositions and methods useful in the preparation of major outer membrane protein ("MOMP") antigens of *Haemophilus influenzae* type b ("Hib"). In particular, the present invention is directed to DNA segments encoding Hib major outer membrane protein antigens, cells transformed with MOMP DNA segments, and the use of these in the preparation of MOMP antigen compositions.

2. Description of the Related Art

*Haemophilus influenzae* type b (Hib) is a leading cause of bacterial meningitis and other invasive infections in infants and young children. Children of the susceptible age range of 6 months to 4 years generally lack antibodies to the Hib capsular polysaccharide, which is a target for antibodies protective against systemic Hib disease. Moreover, children under the age of 2 years typically respond poorly to currently available polysaccharide-based vaccines such as pneumococcal vaccine or the Hib vaccine. For this reason, vaccines containing only capsular polysaccharides are of limited utility in the case of young children, the group most at risk for severe Hib infections.

Although children are generally poor responders to vaccines containing only capsular polysaccharides, it has been reported that children in this age group respond well to protein-based immunogens (1). For example, the outer membrane proteins of Hib appear to be immunogenic in infants, as exemplified by reports of antibody development to Hib cell surface exposed outer membrane proteins following systemic *Haemophilus* disease (2). Moreover, researchers have reported that passive administration of antibodies directed against non-capsular Hib antigens served to protect against experimental Hib bacteremia. (3).

A number of Hib protein components have been studied as possible candidates for the production of passive immunoreagents or in the development of vaccines. While some Hib proteins are either insufficiently antigenic, or their corresponding antibody non-protective (4), one class of Hib proteins have shown some initial promise. These proteins, the so-called major outer membrane proteins or "MOMPs" are proteins that are localized to the Hib outer membrane fractions and thus, are more likely to be exposed or available for antibody binding than are more internally localized proteins. In particular, experiments have been reported wherein antibodies directed against Hib outer membrane proteins appeared to confer protection against bacteremia following intraperitoneal challenge with Hib, whereas antibodies against lipopolysaccharide components lacked protective activity (3). In these experiments, antibodies directed against several outer membrane proteins were detected in the protective immune sera by whole cell radio-immunoprecipitation, suggesting the availability of these antigens on the surface of encapsulated organisms.

In general, the surface-exposed outer membrane proteins of *Haemophilus influenzae* type b studied to date which may have potential for vaccine development, can be characterized as follows—the 98K protein; the P1 protein which is heat modifiable and exhibits an apparent molecular weight of 45–50K after heating at 100° C. in 2% sodium dodecyl sulfate (this protein is also called protein a); the P2 protein which is a porin and which has an apparent molecular weight of 38K–40K (this protein is also called protein b/c or the 39K/38K protein); and the P6 protein which exhibits an apparent molecular weight of 14K–16K.

One of the more interesting Hib MOMP antigens, from a vaccine component or passive immunotherapy standpoint, is the antigen group referred to variously as the 39K (5) or P2 (6) protein species. This protein has been identified as a porin and forms non-covalent complexes with Hib lipopolysaccharide (7,8a). The P2 protein, in fact, demonstrates size heterogeneity from strain to strain, ranging from approximately 38K to 40K, depending on the strain and the method used for determining molecular weight.

The P2 antigen is of particular interest in that studies have demonstrated that polyclonal serum antibodies directed against this antigen are capable of protecting infant rats against Hib bacteremia (6). Unfortunately, while this antigen(s) appears to be useful and desirable from a medical and commercial standpoint, its availability from currently available natural sources is limited. For example, although the protein is a membrane component of Hib strains, its isolation from these strains generally results in limited recoveries.

Thus, there is currently a need for alternative sources from which individual Hib protein antigens and, in particular, selected MOMP antigens such as the P2 antigens, may be obtained and purified. Ideally, such sources should not only allow the preparation of improved anti-Hib antibody and immunogen compositions in terms of ease of preparation and purity, but should also allow isolation of larger, more commercially reasonable quantities.

SUMMARY OF THE INVENTION

Accordingly, in a general and overall sense, the present invention is concerned with the isolation of DNA fragments which are useful in preparation of Hib protein antigens employed in the formulation of vaccines—vaccines particularly suited for use in the vaccination of children and other individuals who respond only poorly to capsular-based vaccines. In more particular terms, the invention is directed to the preparation of a particular class of Hib antigenic protein(s), termed the P2 major outer membrane protein antigen, through recombinant DNA methods.

Preparation of P2 antigen protein(s) is advantageously accomplished in accordance herewith through isolation and use of DNA segments which encode a Hib P2 antigen. P2 antigen-encoding DNA segments of the present invention are defined operationally as segments of DNA, isolated free of total Hib chromosomal or "genomic" DNA such that they may be readily manipulated by recombinant means, the DNA segments encoding protein(s) variously known in the art as the P2 or 39/38K MOMP antigen. Accordingly, as used herein, the phrase "substantially purified DNA segment" refers to a DNA segment isolated free of total chromosomal or genomic DNA and retained in a state rendering it useful for the practice of recombinant techniques, such as DNA in the form of a discrete isolated DNA fragment, or a vector (e.g., plasmid, phage or virus) incorporating such a fragment.

Preferably, P2 DNA sequences in accordance with the present invention will further include genetic control regions which allow the expression of the sequence in a selected recombinant host. Of course, the nature of the control region employed will generally vary depending on the particular use (e.g., cloning host) envisioned. For example, in the preferred recombinant host, *Haemophilus influenzae*, the preferred control region is the homologous control region associated with the structural gene in its natural state. The homologous control region, in fact, may be coisolated directly with the isolation of the P2 structural gene itself through the practice of certain preferred techniques disclosed herein.

Although clearly preferred, it is not believed that useful cloning hosts in accordance herewith are limited to *Haemophilus influenzae* cells. It has been found by the present inventor that *E. coli* is not preferred for cloning and expressing the entire P2 gene, including the functional *Haemophilus* promoter, presumably due to *E. coli*-directed toxicity of the P2 protein. However, it is clearly possible to clone individual fragments from the P2 sequence in *E. coli*. Where one desires to use a host other than *Haemophilus*, it will be advantageous to employ a system other than *E. coli*, such as yeast, CHO, African green monkey, VERO, or the like. Of course, where this is undertaken, it will generally be desirable to bring the P2 gene under the control of a control sequence which is functional in the selected alternative host. The appropriate control sequences, as well as their construction and use, are generally well known in the art as discussed in more detail hereinbelow.

In preferred embodiments, the P2-encoding DNA segments further include DNA sequences, known in the art functionally as origins of replication or "replicons", which allow replication of contiguous sequences by the particular host. Such origins allow the preparation of extrachromosomally localized and replicating chimeric segments or "plasmids" to which P2 DNA sequences are ligated. In more preferred instances, the employed origin is one capable of replication in *Haemophilus influenzae*. However, for more versatility of cloned DNA segments, it may be desirable to alternatively or even additionally employ origins recognized by other host systems whose use is contemplated (such as in a shuttle vector). For example, isolation and use of other replication origins such as the SV40 origin, which may be employed for cloning in a number of higher organisms, are well known. In certain embodiments, the invention may thus be defined in terms of a recombinant transformation vector which includes the P2 gene sequence together with an appropriate replication origin and under the control of selected control regions. Preferred vectors generally include *Haemophilus* vectors such as pHVT1, pDM2, pHCV5 or pGJB103, allowing the cloning of P2 sequences in *Haemophilus* hosts while further providing an antibiotic resistance gene such as Amp$^r$ or Tet$^r$ thus allowing for ready isolation of transformants.

Isolation of *Haemophilus* P2 antigen-encoding DNA sequences is preferably achieved from pathogenic Hib strains in that the antigen product thereof is preferred for vaccine formulation. The preferred method disclosed herein employs the digestion of Hib genomic DNA with the restriction enzyme Pst I, which serves to release a Pst I fragment of about 8 to 10 kb which is thus preferably cloned into a Pst I site (e.g., as contained in the Ampicillin resistance gene, a B-lactamase, in Amp$^r$ cloning vehicles).

However, it will be appreciated by those of skill in the art that the invention is in no way limited to Pst I digestion fragments. For example, *Haemophilus* DNA may be randomly fragmented through the use of partial restriction enzyme digestions In that such digestions are "partial" DNA fragments may be obtained which contain full complements of genes. DNA fragments so-produced are "random" in that under "partial" restriction digestion conditions, not every enzyme recognition site is recognized and cleaved. The fact that a selected restriction enzyme recognition site may be present within, for example, a particular desired coding sequence does not limit the usefulness of "partial" enzyme digestion as a method for fragmenting the DNA because at least a proportion of the population of the DNA fragments will provide a full, uncleaved sequence of the particular gene. Thus, virtually any restriction enzyme may be employed for the generation of *Haemophilus* DNA fragments in accordance with the present invention. Thus, the only limitation generally on the particular restriction enzyme employed for DNA fragmentation is that such enzyme should preferably be compatible with cloning sites present in the particular cloning vehicle employed.

However, it will be appreciated that there is no general requirement that fragments be generated which contain entire coding sequences of the antigen gene. All that is required is to obtain fragments which are sufficiently long to code for polypeptide sequences which are antigenic. In that they are "recognized" antigenically, such polypeptides will at least contain the antigenic determinants ("epitopes") necessary to render such fragments antigenic and hence, such protein fragments may be successfully employed in vaccines or inocula. For the purposes of the present invention, polypeptides which are derivations of full protein. sequences, but which polypeptides nevertheless include immunogenic determinants and are therefore functional in providing an immune response, are considered to be antigenic functional equivalents of the full protein sequences and are thus within the scope of the present invention.

To identify and isolate clones useful in accordance with the invention, one may choose to employ expression screening through the use of an antibody having immunoselecticity for the desired P2 antigen. Expression screening offers the advantage that it only identifies clones which are actively expressing immunoidentifiable protein. Accordingly, if the clone sought will ultimately be the one employed for antigen production, expression screening will likely provide certain advantages.

An alternative or additional screening method would involve the use of cloned or synthetic DNA probes to colony screen transformants. Of course, the most preferred method for such colony screening of transformant clone banks would be through the use of probes cloned as described herein and deposited by the present invention with the American Type Culture Collection in the form of *Haemophilus* strains bearing recombinant plasmid pEJH39-1 (ATCC accession numbers 67574 and 67575). This plasmid contains a Hib Pst I fragment of about 8 to 10 kb which includes the P2 gene and associated homologous control regions.

The foregoing deposits also provide a means to define more preferred aspects of the invention in terms of DNA segments which encode Hib P2 antigen. That is, certain useful DNA segments will hybridize to the P2 DNA inserts of this plasmid (pEJH39-1) at a selected hybridization stringency, and further, will encode a P2 sequence, or a selected portion thereof. Useful hybridization conditions for identifying and defining sequences which encode P2 will generally range from salt conditions of about 0.15 to about 1.0M, temperatures of about 40° C. to 45° C. (where formamide is included), and, preferably, formamide in concentrations ranging from about 20% to 40%, with the most preferred conditions being relatively non-stringent conditions of about 42° C. with 20% formamide and about 0.8M salt.

In certain aspects, the invention therefore concerns nucleic acid molecules comprising sequences corresponding to the P2 gene, or selected subportions thereof, which sequences it is contemplated will have significant utility irrespective of whether they encode antigenic peptides. In such aspects, it is contemplated, for example, that shorter or larger nucleic acid fragments of the P2 gene, prepared synthetically or otherwise, can be employed as hybridization probes. Such probes can readily be employed in a variety of manners, including their use in the detection of pathogenic Hib in selected biological or clinical samples, such as, but not limited to, lesion exudate, cerebrospinal fluid, biopsy specimens or amniotic fluid. By way of useful applications, as well as DNA hybridization techniques, one may wish to refer to references such as Ref. 28 or U.S. Pat. No. 4,358,535, both incorporated herein by reference.

In such embodiments, the nucleic acid molecule selected, whether DNA or RNA, will generally include at least a 10 nucleotide segment of the P2 nucleic acid sequence of Table 2, with the nucleic acid molecule as a whole being capable of forming a detectable stable duplex with said sequence under standard selective nucleic acid hybridization conditions such as those described above, or in references 28–30, incorporated herein by reference. The 10 basepair size is selected as a general lower limit in that at sizes smaller than 10 bases, hybridization stabilization during washing steps following hybridization can become a problem, resulting in much lower signal/noise ratios. Moreover, as the size of the probe decreases to much below 7 to 8 bases, nonspecific hybridization may occur to genes having complementary sequences over short stretches.

In more preferred embodiments, the invention contemplates the preparation and use of nucleic acid molecules whose structure including sequences comprising at least a 17 nucleotide segment of the nucleic acid sequence of FIG. 6A–D. These embodiments recognize that hybridization probes larger than a lower limit of about 10 bases provide more specific stable and overall more dependable hybrid. The only disadvantage to the longer probes is that the expense of preparation can increase somewhat where the fragment is prepared synthetically. However, with advent of DNA synthesizing machines and PCR technology (U.S. Pat. No. 4,683,202, incorporated herein by reference), the expense of preparing larger DNA or RNA probes can be obviated.

In further aspects, the invention is concerned with DNA sequences encoding a P2 protein which includes a sequence of amino acids essentially as shown in Table 2 hereof. This sequence was predicted from a determination of the DNA P2-coding sequence contained in the recombinant insert of plasmid pEJH39-1. The predicted reading frame encodes a protein of about 361 amino acids in length, with the first 20 amino residues forming a leader sequence that is believed to be removed in the mature protein. In any case, natural allelic as well as mutational variations in the DNA of related P2-encoding genes likely exist. For example, it is known that P2 protein from different subspecies exhibit an apparent variation of molecular size, ranging from about 35 to about 39K, when subjected to SDS polyacrylamide gel electrophoresis.

Any such related or variant gene would be expected to have a high degree of sequence similarity to the sequence determined for the P2 gene carried on the insert of plasmid pEJH39-1. Therefore, the pEJH39-1 insert sequence can be used to determine information necessary to prepare probes to identify additional clones bearing related, mutated, modified or even reconstructed DNA segments. The preparation of probes useful for the selection of related sequences, as well as probes useful for other purposes such as conducting in vitro site-directed mutagenesis, are well known in the art and can readily be performed in light of the information disclosed herein.

The sequence information of Table 2 further enables the preparation of discrete antigenic or immunogenic peptides which can themselves be used in antigenic compositions in place of the full P2 antigen itself. The determination of appropriate peptides from within the sequence of the full P2 protein can be made based on either hydrophilicity analyses or, alternatively, based on hydropathy analyses, which can be particular useful in predicting hydrophobic domains (see, Ref.'s 26 and 27). By identifying such regions within the P2 sequence, particularly hydrophilic regions, one can identify short peptidyl regions having particular usefulness in connection with antigenic or immunogenic compositions.

Therefore, in further aspects, the present invention relates to antigenic/immunogenic subfragments of the P2 protein comprising polypeptides of between about 10 and about 30 amino acids in length, characterized by an ability to cross react immunologically with antisera reactive against the P2 antigen. As used herein, the phrase "having an ability to cross react immunologically with antisera specific for the P2 antigen", refers generally to the ability to cross-react immunologically with anti-P2 polyclonal antisera of humans, rabbits, or other animals, or monoclonal antibodies, preferably such as described in reference 10.

Thus, in preferred aspects, the invention concerns antigenic/immunogenic P2 peptide sequences, either derived from recombinant host cells or synthetically prepared "synthetic peptides" of Table 2, corresponding to the individual peptides extending from about the amino acid Gln at position 175 through the amino acid Gly at position 197; the peptide sequence extending from amino acid Gly at position 260 through the amino acid Tyr at position 275; the peptide sequence extending from the amino acid Lys at position 296 through the amino acid Gln at position 311; the peptide sequence extending from the amino acid Ala at position 333 through the amino acid Val at position 353; as well as biologically functional equivalents of the foregoing peptides. It is contemplated that such peptides will find utility both as antigens, for example, in immunologic detection assays, or as immunogens in the formation of vaccines.

In general, as used herein, the phrase "biological functional equivalent" amino acids refer to the fact that the invention contemplates that changes may be made in certain of the foregoing amino acid sequences (e.g., by natural genetic drift, strain or subspecies antigenic variation, or by mutation of the DNA molecules hereof), without necessarily reducing or losing their antigenic/immunogenic identity.

For example, the sequence can be altered through considerations based on similarity in charge (e.g., acidity or basicity charges of the amino acid side group), hydropathic index, or amphipathic score. In general, these broader aspects of the invention are founded in part on the general understanding in the art that certain amino acids may be substituted for other like amino acids without appreciable loss of the peptide's ability to bind to the antibodies, and .thus be recognized antigenically, or alternatively, interact with antibody forming cells to elicit an immune response. Exemplary amino acid substitutions are set forth hereinbelow.

For production of the P2 antigen, the variously cloned P2-encoding DNA segment is preferably employed in the construction of an antigen production host, such as a Hib host which naturally produces the P2 antigen from its own complement of chromosomal genes. By transforming such a host with P2-encoding DNA, a "gene dosaging" effect is observed, with transcription of P2 sequences occurring both chromosomally and extrachromosomally. However, it has been found that transformation of Hib hosts with P2 sequences results in two types of transformants—high and low P2 antigen producers. The generation of "low producers" is presumably due to chromosomal integration of the introduced gene which apparently defeats the "gene dosaging" effect of having both extrachromosomal and chromosomal P2 expression. Accordingly, one will desire to screen transformants, e.g., by observing the gel-staining intensity of P2 expression proteins versus the wild-type Hib host, in order to identify a high P2-producer.

Once a high P2 producing transformant is obtained, the cells are grown and P2 antigen isolated therefrom in substantial purity through the use of techniques disclosed herein. Briefly, cell envelopes of Hib are prepared and extracted with sodium lauryl sarscosinate followed by extraction with sodium deoxycholate. The resultant insoluble material is suspended in Zwittergent 3-14 buffer and the resultant solubilized material containing P2 protein is subjected to column chromatography on a deae-Sephacryl column to obtain relatively purified protein. Of course, it may be desirable to further purify P2 antigen preparations to remove contaminating LPS, if present. However, LPS contamination should not present a problem where non-bacterial hosts are employed for P2 production.

For parenteral administration, the purified P2 antigens or shorter antigenic peptides may be formulated in sesame or peanut oil, aqueous propylene glycol, or in sterile aqueous solutions. Such solutions are typically suitably buffered if necessary and the liquid diluent first rendered isotonic with sufficient saline or glucose. Additionally, stabilizers in the form of, for example, sorbitol or stabilized gelatin may be included. These particular aqueous solutions are particularly well suited for intramuscular and subcutaneous injection, as is generally preferred for vaccination using antigenic preparations.

However, to increase the potential antigenicity, and thereby improve the performance of antigen-containing pharmaceutical preparations, one may additionally desire to include various immunoadjuvants, such as the water-in-oil emulsion developed by Freund or aluminum hydroxide or aluminum phosphate adjuvants. The basic ingredients of light mineral oil (Bayol) and emulsifying agents mixtures such as Aracel (A or C) are available commercially. The antigens are emulsified in either solutions or suspensions of the immunogen (incomplete Freund's adjuvant). Moreover, the addition of mycobacterium (*M. Butyricum, M. tuberculosis*) in small amounts to the suspension (complete Freund's adjuvant) leads to a further enhancement of the immunogenicity of the pharmaceutical vaccines made in accordance with the present invention.

BRIEF DESCRIPTION OF THE DRAWINGS

FIG. 1 is a partial restriction enzyme map of plasmid pEJH39-1 which carries a recombinant insert encoding the P2 coding sequences, as well as associated control and promoter regions. Approximate distances between restriction sites are given in kilobases. The heavy line represents vector DNA. The dotted line represents the approximate location of the P2 coding region with the amino-terminal-coding end shown by "$NH_2$" Abbreviations for restriction sites: B, BamHI; Ps, PstI; R, EcoRI; Pv, PvuII; M, MluI.

FIG. 2 is a Southern blot of restriction enzyme digested chromosomal DNA from Hib strain DL41 (lanes A and C) and DL42 (lanes B and D) probed with a radiolabeled, synthetic oligonucleotide probe for the gene encoding P2 protein. Lanes A and B reflect Pst I digestions, whereas lanes C and D are Eco RI digestions.

FIG. 3 shows a Coumassie blue-stained SDS—10% polyacrylamide slab gel of total cell proteins from the indicated *Haemophilus influenzae* strains. DL42 is a Hib strain; DB117 is the *Haemophilus influenzae* Rd strain used as the host in various cloning experiments; the lane labelled GJB shows strain DB117 containing the cloning vector pGJB103; the lane labelled EJH contains DB117 containing the recombinant plasmid pEJH39-1. The arrows indicate the approximate migration of 39 kD molecular weight.

FIG. 4 is a Western blot of the same set of antigens shown in the SDS-polyacrylamide in FIG. 3, incubated with anti-P2 murine monoclonal antibody 9F5, washed, probed with horseradish peroxidase-coupled goat anti-mouse and rabbit anti-goat immunoglobulin, and developed through the use of 4-chloro-1-naphthol.

FIG. 5 shows a Coumassie blue-stained SDS—10% polyacrylamide slab gel of total cell proteins from the indicated *Haemophilus influenzae* type b strains.

DETAILED DESCRIPTION OF THE PREFERRED EMBODIMENTS

As discussed above, the invention, in a general and overall sense, is concerned with the isolation and purification of DNA segments containing sequences encoding *Haemophilus influenzae* type b (Hib) protein antigens and, in particular, certain of the Hib major outer membrane protein (MOMP) antigens. In accordance herewith, these DNA segments are recombined into useful recombinant vectors which are employed in the production of individual Hib antigens by selected host cells.

Due to its importance, as well as particular difficulties encountered with its cloning, the present disclosure is directed in particular to the isolation, by molecular cloning, of what is termed the 39K MOMP or P2 antigen gene. The difficulties encountered in the construction of recombinant vectors encoding this gene apparently relate to the failure to obtain successful expression of an intact polypeptide in an *E. coli* host. The reason for this is unclear. It could be that the 39K protein itself, which is a porin and which controls the flux of certain substances across the outer membranes, may be extremely toxic to *E. coli* cells. However, it is believed that *E. coli* can likely be successfully employed as a cloning host, for example, where only portions of the P2 coding sequence is being cloned with no expression or where a low copy number vector is employed.

In any event, the present inventor has discovered that the P2 antigen gene cannot readily be cloned in *E. coli* and, in fact, is preferably cloned through the use of *Haemophilus influenzae* cells themselves as hosts. This discovery came about during the development of the invention wherein it was hypothesized that the more appropriate host, in terms of a lack of host-directed P2 toxicity, would be *Haemophilus influenzae* itself. Unfortunately, where the host cell is of the same species as the gene being cloned, novel approaches to clone identification are necessitated.

This problem of identifying appropriately transformed recombinant colonies was solved by an observation by the inventor that certain monoclonal antibodies may generated against the P2 antigen from Hib strains which do not cross-react with the corresponding P2 species from other *Haemophilus influenzae* strains. For example, monoclonal antibody 2F4 binds to the P2 protein of Hib strains and does not bind to the P2 protein of the *Haemophilus influenzae* Rd stain DB117. Thus, through the use of strain-specific anti-P2 antibodies, P2 expression clones are generated and positive clones immunoselected using *Haemophilus influenzae* host strains which produce a non-immunocrossreactive P2 antigen.

The following is a general overview of steps which have been found to work well in the isolation of clones encoding the P2 MOMP antigen. While the following steps are those generally preferred by the present inventor, it will be appreciated by those of skill in the art in light of the disclosure herein, that certain alternative procedures may be employed where desired.

In cloning the P2 gene, it is first generally desirable to obtain a DNA fraction that is enriched in P2 gene sequences relative to total Hib genomic DNA. While not an absolute requirement by any means, enrichment of Hib DNA in P2 sequences prior to cloning greatly reduces the number of negative colonies, thus reducing the overall number of colonies which must be screened. Moreover, the enrichment technique employed herein provides a significant additional advantage in that specific discrete genomic P2 fragments are identified and gel isolated.

In short, enrichment of P2 gene fragments is preferably accomplished by first digesting Hib genomic DNA with a series of restriction enzymes, followed by Southern blot probing of the DNA fragments so-produced with a synthetic oligonucleotide probe to identify P2 sequences. In this manner, the P2 gene is indirectly restriction enzyme site mapped to the extent necessary to identify a single restriction fragment sufficiently large to encompass the entire P2 gene, preferably including control regions. Thus, preparative amounts of genomic Hib DNA can then be digested with the appropriate enzyme, and the identified P2 gene restriction fragment isolated by size fractionation, e.g. by preparative gel isolations.

Following isolation of a P2-enriched Hib DNA fraction, it is next preferable to ligate the enriched DNA with a selected recombinant vector. The preferred host is *H. influenzae* itself. More specifically, a *Haemophilus influenzae* Rd strain designated DBl17 was used for this purpose. This particular *Haemophilus influenzae* strain is recombination deficient, a genetic trait facilitates the cloning of chromosomal DNA fragments.

A number of suitable *Haemophilus* plasmids are known in the art and may be employed, for example, as exemplified by the amp plasmid pRSF0885 (15) or the *E. coli/Haemophilus influenzae* shuttle vectors pHCV5 or pHVTI (8, incorporated herein by reference) or the *E. coli/ Haemophilus influenzae* shuttle vector pDM2(9). The particular vector employed by the present inventor and preferred for practice in accordance herewith, pGJB103, is a modified version of the plasmid pHVTI, wherein the 2.3 kb Ava I/Sph I site has been deleted, and a Bgl II linker inserted at the Ssp I site of the B-lactamase gene in its untranslated leader region.

In addition to prokaryotes such as *Haemophilus influenzae*, it is believed that eukaryotic microbes, such as yeast cultures may also be used for cloning. *Saccharomyces cerevisiae*, or common baker's yeast is the most commonly used among eukaryotic microorganisms, although a number of other strains are commonly available. For expression in *Saccharomyces*, the plasmid YRp7 (17, 18), for example, is commonly used. This plasmid already contains the trp1 gene which provides a selection marker for a mutant strain of yeast lacking the ability to grow in tryptophan, for example ATCC No. 44076 or PEP4-1 (19). The presence of trpl lesion as a characteristic of the yeast host cell genome then provides an effective environment for detecting transformation by growth in the absence of tryptophan.

Suitable promoting sequences in yeast vectors include the promoters for 3-phosphoglycerate kinase (20), such as enolase, glyceraldehyde-3-phosphate dehydrogenase, hexokinase pyruvate decarboxylase, phosphofructokinase, glucose-6-phosphate isomerase, 3-phosphoglycerate mutase, pyruvate kinase, triosephosphate isomerase, phosphoglucose isomerase, and glucokinase. Other promoters, which have the additional advantage of transcription controlled by growth conditions are the promoter regions for alcohol dehydrogenase 2, isocythochrome C, acid phosphatase, degradative enzymes associated with nitrogen metabolism, and the aforementioned glyceraldehyde-3-phosphate dehydrogenase, and enzymes responsible for maltose and galactose utilization. Any plasmid vector containing a promoter capable of functioning in yeast cells, origin of replication and termination sequences is believed to be suitable.

In addition to microorganisms, cultlures of cells derived from multicellular organisms may also be useful. In principle, any such cell culture is workable, whether from vertebrate or invertebrate culture. However, interest has been greatest in vertebrate cells, and propogation of vertebrate cells in culture (tissue culture) has become a routine procedure in recent years (22). Examples of such useful host cell lines are VERO and HeLa cells, Chinese hamster ovary (CHO) cell lines, and W138, BHK, COS-7 and MDCK cell lines. Expression vectors for such cells ordinarily include an origin of replication, a promoter located in front of the gene to be expressed, along with any necessary ribosome binding sites, RNA splice sites, polyadenylation site, and transcriptional terminator sequences.

For use in mammalian cells, the control functions on the expression vectors are often provided by viral material. For example, commonly used promoters are derived from polyoma, Adenovirus 2, and most frequently Simian Virus 40 (SV40). The early and late promoters of SV40 virus are particularly useful because both are obtained easily from the virus as a fragment which also contains the SV40 vital origin of replication (23). Smaller or larger SV40 fragments may also be used, provided there is included the approximately 250 bp sequence extending from the Hind III site toward the Bgl I site located in the viral origin of replication. Further, it is also possible, and often desirable, to utilize promoter or control sequences normally associated with the desired gene sequence, provided such control sequences are compatible with the host cell systems.

An origin of replication may be provided either by construction of the vector to include an exogenous origin, such as may be derived from SV40 or other viral (e.g., Polyoma, Adeno, VSV, BPV, etc.) source, or may be provided by the host cell chromosomal replication mechanism. If the vector is integrated into the host cell chromosome, the latter is often sufficient.

Where *Haemophilus influenzae* cells are employed as hosts, one can employ virtually any strain and obtain successful replication and expression of the P2 gene. Of course, as discussed, for case of initial clone identification, one will want to employ a strain that does not produce the particular P2 sought. For the preparation of immunoreagents, whether passive or immunogenic, one will generally desire to clone a P2 variant from a Hib strain. Thus, in terms of the cloning host, one would want to employ a strain whose P2 protein can be immunologically distinguished from that of the Hib P2.

It has been found that commonly available lab strains such as DB117, and other Rd strains of *Haemophilus influenzae* (such as KW20) may be employed quite readily as hosts. This is true in that monoclonal antibodies (e.g., 2F4) may be prepared which are reactive with the P2 protein of Hib strains, yet is not reactive with the P2 proteins of *Haemophilus influenzae* Rd strains. Therefore, an Rd strain of *Haemophilus influenzae* unreactive with monoclonal antibody 2F4 can be a host for cloning experiments involving the gene encoding the P2 of Hib strains. Ideally, the Rd strain would also be recombination-deficient like DB117. The source of chromosomal DNA for the cloning experiment can be any Hib strain whose P2 protein is reactive with monoclonal antibody 2F4; the present inventor has found that 117 of 117 Hib strains react with this particular antibody (10).

Following transformation of host *Haemophilus influenzae* cells with recombinant plasmid, the transformants are preferably screened by an expression screening assay, numerous of which are known to those skilled in the art and can be used in the practice of the invention. The present inventor prefers to employ a modified expression screening technique wherein plated colonies are first imprinted onto sterile adsorbent sheet, such as Whatman #40, and the sheet contacted with the desired anti-P2 antibody under conditions appropriate for the formation of specific immunocomplexes. After washing, the sheet is then contacted with a labeled second antibody and immuno-positive colonies identified by autoradiography. Positive colonies can then be further screened by single colony isolation, restriction enzyme digestion and additional confirming immunoassays performed if desired.

Once a positive clone has been isolated, plasmid DNA may be prepared in quantity, just as in a typical *E. coli* cloning host, and isolated to relative purity by techniques such as column adsorption or buoyant density centrifugation. For use in the generation of P2 protein preparation it is preferred to express the cloned gene in a Hib host that produces the P2 MOMP antigen endogenously, allowing the "gene dosaging" effect of having both an active chromosomal as well as extra-chromosomal gene. Of course, the most convenient host in this regard will typically be the Hib strain which provided the starting genomic DNA, or a similar strain. A preferred vector would be the *Haemophilus influenzae* organism from which the capsular polysaccharide is derived.

Once this transformation of a selected production host has been accomplished, if desired, isolation of P2 MOMP antigen is isolated by a relatively easy series of steps, based generally on the isolation procedure described by Munson et al. (6). Briefly, cell envelopes of Hib are prepared and extracted with sodium lauryl sarscosinate followed by extraction with sodium deoxycholate. The resultant insoluble material is suspended in Zwittergent 3-14 buffer and the resultant solubilized material containing P2 protein is subjected to column chromatography on a DEAE-Sephacryl column to obtain relatively purified protein.

As mentioned, in certain aspects, the DNA sequence information provided by the invention (see Table 2) allows for the preparation of relatively short DNA (or RNA) sequences having the ability to specifically hybridize to gene sequences of the P2 gene. In these aspects, nucleic acid probes of an appropriate length are prepared based on a consideration of the natural sequence shown in Table 2, or derived from flanking regions of the P2 gene, such as regions downstream of the gene as found in plasmid pEJH39-1 (see FIG. 1 and Example II below). The ability of such nucleic acid probes to specifically hybridize to the P2 gene sequences lend them particular utility in a variety of embodiments. Most importantly, the P2-derived probes can be used in a variety of diagnostic assays for detecting the presence of pathogenic organisms in a given sample. However, either uses are envisioned, including the use of the sequence information for the preparation of mutant species primers, or primers for use in preparing other genetic constructions.

To provide certain of the advantages in accordance with the invention, the preferred nucleic acid sequence employed for hybridization studies or assays includes sequences that are complementary to at least a 10 to 20, or so, nucleotide stretch of the sequence shown in Table 2. A size of at least 10 nucleotides in length helps to ensure that the fragment will be of sufficient length to form a duplex molecule that is both stable and selective. Molecules having complementary sequences over stretches greater than 10 bases in length are generally preferred, though, in order to increase stability and selectivity of the hybrid, and thereby improve the quality and degree of specific hybrid molecules obtained. Thus, one will generally prefer to design nucleic acid molecules having P2 gene-complementary stretches of 15 to 20 nucleotides, or even longer where desired. Such fragments may be readily prepared by, for example, directly synthesizing the fragment by chemical means, by application of nucleic acid reproduction technology, such as the PCR technology of U.S. Pat. No. 4,603,102, or by introducing selected sequences into recombinant vectors for recombinant production.

In that the P2 protein is indicative of pathogenic Hib species, the present invention will find particular utility as the basis for diagnostic hybridization assays for detecting P2-specific RNA or DNA in clinical samples. Exemplary clinical samples that can be used in the diagnosis of infections are thus any samples which could possibly include pathogenic Hib nucleic acid, including biological or clinical samples or the like. A variety of hybridization techniques and systems are known which can be used in connection with the hybridization aspects of the invention, including diagnostic assays such as those described in Falkow et al., U.S. Pat. No. 4,358,535.

Accordingly, the nucleotide sequences of the invention are important for their ability to selectively form duplex molecules with complementary stretches of the P2 gene. Depending on the application envisioned, one will desire to employ varying conditions of hybridization to achieve varying degree of selectivity of the probe toward the target sequence. For applications requiring a high degree of selectivity, one will typically desire to employ relatively stringent conditions to form the hybrids, for example, one will select relatively low salt and/or high temperature conditions, such as provided by 0.02M–0.15M NaCl at temperatures of 50° C. to 70° C. These conditions are particularly selective, and tolerate little, if any, mismatch between the probe and the template or target strand.

Of course, for some applications, for example, where one desires to prepare mutants employing a mutant primer strand hybridized to an underlying template, less stringent hybridization conditions are called for in order to allow formation of the heteroduplex. In these circumstances, one would desire to employ conditions such as 0.15M–0.9M salt, at temperatures ranging from 20° C. to 55° C. In any case, it is generally appreciated that conditions can be rendered more stringent by the addition of increasing amounts of formamide, which serves to destabilize the hybrid duplex in the same manner as increased temperature. Thus, hybridization conditions can be readily manipulated, and thus will generally be a method of choice depending on the desired results.

In clinical diagnostic embodiments, nucleic acid sequences of the present invention are used in combination with an appropriate means, such as a label, for determining hybridization. A wide variety of appropriate indicator means are known in the art, including radioactive, enzymatic or other ligands, such as avidin/biotin, which are capable of giving a detectable signal. In preferred diagnostic embodiments, one will likely desire to employ an enzyme tag such as urease, alkaline phosphatase or peroxidase, instead of radioactive or other environmental undesirable reagents. In the case of enzyme tags, colorimetric indicator substrates are known which can be employed to provide a means visible to the human eye or spectrophotometrically, to identify specific hybridization with pathogen nucleic acid-containing samples.

In general, it is envisioned that the hybridization probes described herein will be useful both as reagents in solution hybridization as well as in embodiments employing a solid phase. In embodiments involving a solid phase, the test DNA (or RNA) from suspected clinical samples, such as exudates, body fluids (e.g., amniotic fluid cerebrospinal fluid) or even tissues, is adsorbed or otherwise affixed to a selected matrix or surface. This fixed, single-stranded nucleic acid is then subjected to specific hybridization with selected probes under desired conditions. The selected conditions will depend on the particular circumstances based on the particular criteria required (depending, for example, on the G+C contents, type of target nucleic acid, source of nucleic acid, size of hybridization probe, etc.). Following washing of the hybridized surface so as to remove nonspecifically bound probe molecules, specific hybridization is detected, or even quantified, by means of the label.

As noted above, particular advantages of the invention may be realized through the preparation of synthetic peptides which include epitopic/immunogenic core sequences. These epitopic core sequences are identified herein in particular aspects as hydrophilic regions of the P2 ahtigen. It is proposed that these regions represent those which are most likely to promote T-cell or B-cell stimulation, and, hence, elicit specific antibody production. An epitopic core sequence, as used herein, is a relatively short stretch of amino acids that is "complementary" to, and therefore will bind, antigen binding sites on anti-P2 antibodies. It will be understood that in the context of the present disclosure, the term "complementary" refers to amino acids or peptides that exhibit an attractive force towards each other. Thus, epitope core sequences of the present invention may be operationally defined in terms of their ability to compete with or even displace the binding of the P2 antigen with anti-P2 antisera.

In general, the size of the polypeptide antigen is not believed to be particularly crucial, so long as it is at least large enough to carry the identified core sequence or sequences. The smallest core sequence identified by the present disclosure is on the order of about 15 amino acids in length. Thus, this size will generally correspond to the smallest peptide antigens prepared in accordance with the invention. However, the size of the particular core sequences identified by the invention ranges from 15 to 22 amino acids in length. Thus, the size of the antigen may be larger where desired, so long as it contains the basic epitopic core sequence.

Accordingly, through the use of computerized peptide sequence analysis program (DNAStar Software, DNAStar, Inc., Madison, Wis.), The inventor has identified particular hydrophilic peptidyl regions of the P2 antigen which, due to their hydrophilicity, are believed to constitute epitopic core sequences comprising particular epitopes of the protein. These epitopic core sequences are illustrated by reference to Table 2 as corresponding to the individual peptides extending from about the amino acid Gln at position 175 through the amino acid Gly. at position 197; the peptide sequence extending from amino acid Gly at position 260 through the amino acid Tyr at position 275; the peptide sequence extending from the amino acid Lys at position 296 through the amino acid Gln at position 311; the peptide sequence extending from the amino acid Ala at position 333 through the amino acid Val at position 353; as well as biologically functional equivalents of the foregoing peptides, as explained in more detail below.

Syntheses of the foregoing sequences, or peptides which include the foregoing within their sequence, is readily achieved using conventional synthetic techniques such as the solid phase method (e.g., through the use of commercially available peptide synthesizers such as an Applied Biosystems Model 430A Peptide Synthesizer). Peptide antigens synthesized in this manner may then be aliquoted in predetermined amounts and stored in conventional manners, such as in aqueous solutions or, even more preferably, in a powder or lyophilized state pending use.

In general, due to the relative stability of the peptides of the invention, it is believed that they may be readily stored in aqueous solutions for fairly long periods of time if desired, e.g., up to six months or more, in virtually any aqueous solution likely without appreciable degradation or loss o antigenic activity. However, where extended aqueous storage is contemplated it will generally be desirable to include agents including buffers such as Tris or phosphate buffers to maintain a pH of 7.0 to 7.5. Moreover, it amy be desirable to include agents which will inhibit microbial growth, such as sodium azide or Merthiolate ®. For extended storage in an aqueous state it will be desirable to store the solutions at 4° C., or more preferably, frozen. Of course, where the peptide(s) are stored in a lyophilized state, they may be stored virtually indefinitely, e.g., in metered aliquots that may be rehydrated with a predetermined amount of water (preferably distilled) or buffer prior to use.

As noted above, it is believed that various modification and changes may be made in the structure of the P2 antigen, or antigenic/immunogenic subportions thereof, and still obtain a molecule having like or otherwise desirable characteristics.

For example, certain amino acids may be substituted for other amino acids in a protein structure without appreciable loss of interactive binding capacity with complementary structures such as antigen-binding regions of antibodies (or, e.g., binding sites on receptor molecules). It is thus hypothesized by the present inventor that various changes may be made in the sequence of the antigenic peptides without appreciable loss of their antibody-binding, or P2 antigen competing, activity.

The importance of the hydropathic index of amino acids in conferring interactive biologic function on a protein has been discussed generally by Kyte et al. (27), wherein it is found that certain amino acids may be substituted for other amino acids having a similar hydropathic index or core and still retain a similar biological activity. As displayed in the table below, amino acids are assigned a hydropathic index on the basis of their hydrophobicity and charge characteristics. It is believed that the relative hydropathic character of the amino acid determines the secondary structure of the resultant protein, which in turn defines the interaction of the protein with substrate molecules.

TABLE I

| Amino Acid | Hydropathic Index |
|---|---|
| Isoleucine | 4.5 |
| Valine | 4.2 |
| Leucine | 3.8 |
| Phenylalanine | 2.8 |
| Cysteine/cystine | 2.5 |
| Methionine | 1.9 |
| Alanine | 1.8 |
| Glycine | −0.4 |
| Threonine | −0.7 |
| Tryptophan | −0.9 |
| Serine | −0.8 |

TABLE I-continued

| Amino Acid | Hydropathic Index |
|---|---|
| Tyrosine | −1.3 |
| Proline | −1.6 |
| Histidine | −3.2 |
| Glutamic Acid | −3.5 |
| Glutamine | −3.5 |
| Aspartic Acid | −3.5 |
| Asparagine | −3.5 |
| Lysine | −3.9 |
| Arginine | −4.5 |

Thus, for example, isoleucine, which has a hydropathic index of +4.5, can be substituted for valine (+4.2) or leucine (+3.8), and still obtain a protein having similar biologic activity. Alternatively, at the other end of the scale, lysine (−3.9) can be substituted for arginine (−4.5), and so on. Accordingly, these amino acid substitutions are generally based on the relative similarity of R-group substituents, for example, in terms of size, electrophilic character, charge, and the like.

Site-specific mutagenesis is a technique useful in the preparation of individual peptides, or biologically functional equivalent proteins or peptides, derived from the P2 sequence, through specific mutagenesis of the underlying DNA. The technique further provides a ready ability to prepare and test sequence variants, for example, incorporating one or more of the foregoing considerations, by introducing one or more nucleotide sequence changes into the DNA. Site-specific mutagenesis allows the production of mutants through the use of specific oligonucleotide sequences which encode the DNA sequence of the desired mutation, as well as a sufficient number of adjacent nucleotides, to provide a primer sequence of sufficient size and sequence complexity to form a stable duplex on both sides of the deletion junction being traversed. Typically, a primer of about 17 to 25 nucleotides in length is preferred, with about 5 to 10 residues on both sides of the junction of the sequence being altered.

In general, the technique of site-specific mutagenesis is well known in the art as exemplified by publications such as reference 31, incorporated herein by reference. As will be appreciated, the technique typically employs a phage vector which exists in both a single stranded and double stranded form. Typical vectors useful in site-directed mutagenesis include vectors such as the M13 phage, for example, as disclosed by reference 32, incorporated herein by reference. These phage are readily commercially available and their use is generally well known to those skilled in the art.

In general, site-directed mutagenesis in accordance herewith is performed by first obtaining a single-stranded vector which includes within its sequence a DNA sequence which encodes the P2 antigen. An oligonucleotide primer bearing the desired mutated sequence is prepared, generally synthetically, for example by the method of reference 33. This primer is then annealed with the singled-stranded vector, and subjected to DNA polymerizing enzymes such as E. coli polymerase I Klenow fragment, in order to complete the synthesis of the mutation-bearing strand. Thus, a heteroduplex is formed wherein one strand encodes the original non-mutated sequence and the second strand bears the desired mutation. This heteroduplex vector is then used to transform appropriate cells such as E. coli cells and clones are Iselected which include recombinant vectors bearing the mutated sequence arrangement.

It is proposed that the P2 antigenic peptides of the invention will find utility as immunogens in connection with vaccine development, or as antigens in immunoassays for the detection of anti-P2 antigen-reactive antibodies. Turning first to immunoassays, in their most simple and direct sense, preferred immunoassays of the invention include the various types of enzyme linked immunosorbent assays (ELISAs) known to the art. However, it will be readily appreciated that utility is not limited to such assays, and useful embodiments include RIAs and other non-enzyme linked antibody binding assays or procedures.

In the preferred ELISA assay, peptides incorporating the P2 antigen sequences are immobilized onto a selected surface, preferably a surface exhibiting a protein affinity such as the wells of a polystyrene microtiter plate. After washing to remove incompletely adsorbed material, one will desire to bind or coat a nonspecific protein such as bovine serum albumin (BSA) or casein onto the well that is known to be antigenically neutral with regard to the test antisera. This allows for blocking of nonspecific adsorption sites on the immobilizing surface and thus reduces the background caused by nonspecific binding of antisera onto the surface.

After binding of antigenic material to the well, coating with a non-reactive material to reduce background, and washing to remove unbound material, the immobilizing surface is contacted with the antisera or clinical or biological extract to be tested in a manner conducive to immune complex (antigen/antibody) formation. Such conditions preferably include diluting the antisera with diluents such as BSA, bovine gamma globulin (BGG) and phosphate buffered saline (PBS)/Tween. These added agents also tend to assist in the reduction of nonspecific background. The layered antisera is then allowed to incubate for from 2 to 4 hours, at temperatures preferably on the order of 25° to 27° C. Following incubation, the antisera-contacted surface is washed so as to remove nonimmunocomplexed material. A preferred washing procedure includes washing with a solution such as PBS/Tween, or borate buffer.

Following formation of specific immunocomplexes between the test sample and the bound antigen, and subsequent washing, the occurrence and even amount of immunocomplex formation may be determined by subjecting same to a second antibody having specificity for the first. To provide a detecting means, the second antibody will preferably have an associated enzyme that will generate a color development upon incubating with an appropriate chromogenic substrate. Thus, for example, one will desire to contact and incubate the antisera-bound surface with a urease or peroxidase-conjugated IgG for a period of time and under conditions which favor the development of immunocomplex formation (e.g., incubation for 2 hours at room temperature in a PBS-containing solution such as PBS-Tween).

After incubation with the second enzyme-tagged antibody, and subsequent to washing to remove unbound material, the amount of label is quantified by incubation with a chromogenic substrate such as urea and bromocresol purple or 2,2'-azino-di-(3-ethyl-benzthiazoline-6-sulfonic acid [ABTS] and $H_2O_2$, in the case of peroxidase as the enzyme label. Quantification is then achieved by measuring the degree of color generation, e.g., using a visible spectra spectrophotometer.

Immunogenic compositions, suitable for use as a vaccine, may be prepared most readily directly from P2 antigens purified in the foregoing manner. For example, one may desire to formulate immunogen compositions using the P2 antigen preparation derived by gel exclusion chromatography of the recombinant Hib proteins. A further preferred embodiment would involve Hib P2 protein not by itself, but instead covalently coupled to Hib capsular polysaccharide or other bacterial capsular polysaccharide, in order to increase the immunogenicity of said capsular polysaccharide in vaccine preparation. (25)

The preparation of vaccines which contain peptide sequences as active ingredients is generally well understood in the art, as exemplified by U.S. Pat. Nos. 4,608,251; 4,601,903, 4,599,321; 4,599,230; 4,596,792; and 4,578,770, all incorporated herein by reference. Typically, such vaccines are prepared as injectables: either as liquid solutions or suspension, solid forms suitable for solution in, or suspension in, liquid prior to injection may also be prepared. The preparation may also be emulsified. The active immunogenic ingredient is often mixed with excipients which are pharmaceutically acceptable and compatible with the active ingredient. Suitable excipients are, for example, water, saline, dextrose, glycerol, ethanol, or the like and combinations thereof. In addition, if desired, the vaccine may contain minor amounts of auxiliary substances such as wetting or emulsifying agents, pH buffering agents, or adjuvants which enhance the effectiveness of the vaccine.

The proteins may be formulated into the vaccine as natural or salt forms. Pharmaceutically acceptable salts, include the acid addition salts (formed with the free amino groups of the peptide) and which are formed with inorganic acids such as, for example, hydrochloric or phosphoric acids, or such organic acids as acetic, oxalic, tartaric, mandelic, and the like. Salts formed with the free carboxyl groups may also be derived from inorganic bases such as, for example, sodium, potassium, ammonium, calcium, or ferric hydroxides, and such organic bases as isopropylamine, trimethylamine, 2-ethylamino ethanol, histidine, procaine, and the like.

The vaccines are administered in a manner compatible with the dosage formulation, and in such amount as will be therapeutically effective and immunogenic. The quantity to be administered depends on the subject to be treated, capacity of the individual's immune system to synthesize antibodies, and the degree of protection desired. Precise amouhts of active ingredient required to be administered depend on the judgment of the practitioner and are peculiar to each individual. Suitable regimes for initial administration and booster shots are also variable, but are typified by an initial administration followed by subsequent inoculations or other administrations.

Various methods of achieving adjuvant effect for the vaccine includes use of agents such as aluminum hydroxide or phosphate (alum), commonly used as 0.05 to 0.1 percent solution in phosphate buffered saline, admixture with synthetic polymers of sugars (Carbopol) used as 0.25 percent solution, or aggregation of the protein in the vaccine by heat treatment with temperatures ranging between 70° to 101° C. for 30 second to 2 minute periods, respectively. Aggregation by reactivating with pepsin treated (Fab) antibodies to albumin, mixture with bacterial cells such as *C. parvum* or endotoxins or lipopolysaccharide components of gram-negative bacteria, emulsion in physiologically acceptable oil vehicles such as mannide mono-oleate (Aracel A) or emulsion with 20 percent solution of a perfluorocarbon (Fluosol-DA) used as a block substitute, may also be employed.

In many instances, it will be desirable to have multiple administrations of the vaccine, usually not exceeding six vaccinations, more usually not exceeding four vaccinations and preferably one or more, usually at least about three vaccinations. The vaccinations will normally be at from two to twelve week intervals, more usually from three to five week intervals. Periodic boosters at intervals of 1–5 years, usually three years, will be desirable to maintain protective levels of the antibodies. The course of the immunization may be followed by assays for antibodies for the supernatant antigens. The assays may be performed bylabelling with conventional labels, such as radionuclides, enzymes, fluorescers, and the like. These techniques are well known and may be found in a wide variety of patents, such as U.S. Pat. Nos. 3,791,932, 4,174,384 and 3,949,064, as illustrative of these types of assays.

The following examples are included to demonstrate with more particularity the techniques and methodology employed by the present inventor to clone and express the P2 gene of Hib. It should be appreciated that, as such, these examples are exemplary only and that a variety of possible ways of achieving the same end will be apparent to those of skill in the art in light of the following disclosure. For example, while the restriction enzyme Pst I was employed to generate a Hib chromosomal DNA fragment of about 8–10 kb which contained the P2 gene, it's clear that the invention is not limited to such a fragment. Clearly, virtually any known restriction enzyme can be successfully employed so long as the Hib genomic DNA can be "partially digested" to provide randomly "sheared" fragments. Numerous other modification will likely be apparent as well and all such modifications are intended to be within the spirit and scope of the invention.

EXAMPLE I

Identification of Hib Protein P2 Gene Fragments

Bacterial Strains

Two different Hib strains, DL41 and DL42, were used in most of the experiments detailed herein. Both of these strains were isolated from infants with Hib meningitis. Strain DB117, used as a cloning host, is a recombination-deficient *Haemophilus influenzae* Rd strain (24). Media and growth conditions for *Haemophilus influenzae* strains were as described by Holmans et al. (11), except that tetracycline hydrochloride (5 ug/ml) was included in the growth medium for certain experiments.

Isolation of Hib Genomic DNA

Genomic DNA was isolated from strains DL41 and DL42 generally by the method of Bricker, et al. (12). Briefly, Hib cells were lysed with sodium dodeoyl sulfate. The lysate was digested with Pronase and extracted with phenol: chloroform and then with chloroform, RNAse-treated, extracted again as before, and the chromosomal DNA was precipitated with ethanol.

Southern Blot Screening Hib Genomic DNA Fragments

In order to identify Hib DNA fragments which encode P2 gene sequences, Hib genomic DNA was first digested with a selected restriction enzyme, the restriction fragments separated by agarose gel electrophoresis, the gel-fractionated fragments blotted to nitrocellulose and the resultant Southern blot probed with a labeled oligonucleotide probe which correspond to the deduced amino terminus DNA sequence of the P2 gene.

To obtain the amino-terminal sequence of the P2 protein; the P2 protein of Hib strain DL42 was isolated to relative homogeneity by the method of Munson et al. (6). The NH$_2$-terminal amino acid sequence of this protein was determined to be NH$_2$—ALA—VAL—VAL—TyR—ASN—ASN—GLU—GLy—THR—ASN—VAL—GLU—LEU—GLY—GLY—ARG—LEU—SER—ILE—iLE. An oligonucleotide probe comprised of 59 bases encoding these first twenty amino acids from the NH$_2$-terminus of the 39K protein was designed using *E. coli* codon usage assignments and synthesized. The nucleotide sequence of this oligonucleotide probe was GCT GTT GTT TAT AAC AAC GAA GGT ACC AAC GTT GAA CTG GGT GGT CGT CTG TCT ATC AT.

For preparation of the Southern blots, about 3 ug genomic DNA from DL42 and DL41 was digested to completion with Pst I or Eco RI and the digestion products electrophoresed in a 1% agarose gel in a horizontal electrophoresis system. The gel was then transferred to nitrocellulose by the method of Southern (13), and the resultant nitrocellulose blot subjected to hybridization with $^{32}$P-labeled oligonucleotide probe as described by Southern (13) and modified by Swancutt, et al. (14).

Figures 2, 3:
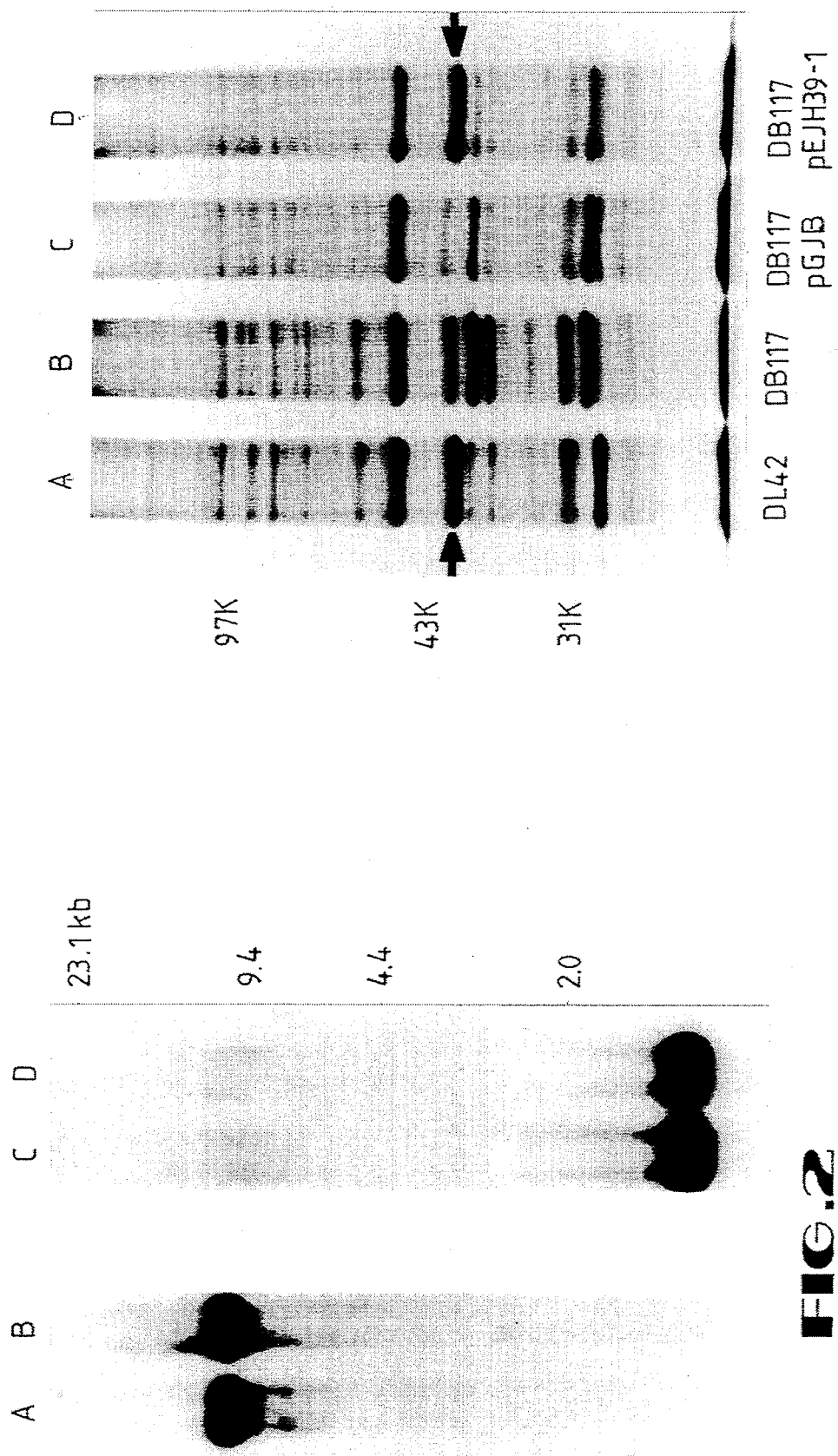

The results of this experiment are shown in FIG. 2. It will be appreciated that in both strains DL41 and DL42 the synthetic hybridization probe recognized a Pst I fragment having an apparent length of approximately 10 kb, (columns A and B, DL41 and DL42, resp.) and also an Eco RI fragment of about 1.5 kb (columns C and D, DL41 and DL42, resp.). Due to its larger size, the Pst I fragment was targeted for cloning.

EXAMPLE II

Cloning and Isolation of P2 Gene Sequences

To clone the 10 kb Pst I P2 gene fragment, a complete Pst I digest of Hib strain DL42 chromosomal DNA was prepared by digesting 375 ug of DNA with about 1,000 units of Pst I for 2 hours at 37° C. The digested DNA was then electrophoresed in a 1% agarose slab gel. Through the use of size markers, the regions of the gel corresponding to DNA fragments of about 8 to 15 kb in length were excised, the agarose strips were homogenized and the DNA eluted from the gel fragments using dilute Tris-EDTA buffer at 55° C.

The eluted DNA was purified by passage over a NACS column (Bethesda Research Labs, Bethesda, Md.), and ligated with Pst I-linearized plasmid pGJB103 (a derivative of pHVT1 as discussed above, see ref. 8). Briefly, ligation was accomplished by incubating 1.5 ug of the sized DNA fragments with 0.43 ug of Pst I-cut and alkaline phosphatase-treated pGJB103 plasmid, ATP, and T4 DNA ligase. After ligation, the DNA was concentrated by ethanol precipitation and s01ubilization in a minimal volume of sterile PBS.

This mixture was used to transform DB117 cells as follows. On day 1, 10 ml of brain heart infusion broth supplemented with levinthai base (5) (BHIs) in a large culture tube was inoculated with DB117 and placed in an ice bath starter in the late afternoon. The tray containing the ice water and culture tube was placed in a 370 incubator room. The ice bath starter was used to keep the culture cold until the middle of the night when the ice melts and the temperature of the culture rises to 37° C., thus permitting rapid growth. The next morning, 1.0 ml of ice bath starter culture was inoculated into 19.0 mls of BHI in a side arm flask and shaken at 37° until a cell density corresponding to a Klett colorimeter reading of 95 units (green filter) was observed (blank=25 units). 10 mls of cells were then pipetted into a 17×100 mm snap cap plastic tube and incubated for an additional 75 minutes at 37° without shaking. 0.2 mls of these cells were then transferred to a new snap cap tube and 1.8 ml of PBS containing 900 ug/ml lactate (pH 7.2) was added and the mixture incubated for an additional 65 minutes at 30° C. without shaking.

The entire DNA ligation mixture was then added with gentle but thorough mixing. This was then incubated for 30 minutes at 30° C. without shaking. After 30 minutes, 1.35 ml of warmed (37° C.) 80% glycerol was added with thorough mixing and allowed to stand for 10 minutes at room temperature. The entire mixture was then pipetted into 10 mls BHIs in a 125 ml flask (prewarmed to 37° C.), and the flask shaken at 37° C. for 3 hours. At this time, the entire culture was pipetted into a sterile centrifuge tube and spun for 10 minutes at 6,700 xg at 4° C. The resultant pellet was resuspended in 1 ml BHIs and 0.1 ml portions of this were spread on 10 BHIs agar plates containing 5 ug/ml tetracycline hydrochloride to select for plasmid containing transformants and these plates were incubated at 37° C. in a candle extinction jar for 18-20 hours.

The foregoing transformation experiment provided a total of 364 tetracycline-resistant colonies, which colonies were then expression screened to identify P2-expressing transformants as follows. Sterile Whatman #40 filter paper disks were overlayed onto the plated colonies removed and allowed to air-dry for one hour at 37° (the plates were then stored in the refrigerator to maintain the viability of the *Haemophilus influenzae* cells). The air-dried filters were then soaked in PBS containing 2% normal rabbit serum for one hour at 4° C. with gentle rocking to block non-specific binding sites on the filter paper.

After soaking, the filters were covered with about 13 mls of monoclonal antibody 2F4 culture supernatant, and allowed to incubate in the cold room for two hours with gentle rocking. This monoclonal antibody recognizes specifically the P2 antigen from DL42 (and DL41) cells but does not recognize the corresponding antigen from DB117 cells, used as a host in the present cloning experiments. The preparation and characteristics of 2F4 monoclonal antibody is described by Gulig et al., reference 10, incorporated herein by reference. Briefly, This antibody recognizes an epitope in the P2 protein of 117 of 117 Hib strains tested to date and does not recognize the P2 protein of the *Haemophilus influenzae* strain DB117.

After 2 hours incubation, the antibody mixture was decanted and the filters washed with 4×30' washes in PBS with 2% normal calf serum. The washed filters were then incubated with affinity purified and radioiodinated goat anti-mouse IgG and with gentle rocking in the cold room overnight, followed by 4 additional washes, 30' each, using PBS-2% calf serum. The filters were then dried and autoradiographed.

From the total of 364 colonies screened, 10 colonies were identified as being reactive with the Hib P2-specific monoclonal antibody. These 10 colonies were then restreaked for purification by single colony isolation and retested in a colony blot radioimmunoassay with monoclona antibody 2F4 as above. ,All colonies retested positive.

One clone, designated DB117 (pEJH39-1), was selected for further study and found to contain an 8-10 kb Pst I insert, which insert was found to contain the entire P2 gene. The plasmid pEJH39-1 was subjected to restriction enzyme analyses, and a restriction enzyme map generated as shown in FIG. 1. Moreover, the coding sequence of the P2 gene (shown by the dotted line in FIG. 1) carried by plasmid pEJH39-1 was subjected to DNA sequence analyses, and the result obtained from that work is shown in FIG. 6. The following examples present confirmatory experiments as well as the construction of a high level P2-producing line through the use of DL42 as a host for pEJH39-1 expression.

Clone DB117 (pEJH39-1) was deposited with the American Type Culture Collection on Dec. 8, 1987, under the provisions of the Budapest Treaty, and accorded accession number 67574.

EXAMPLE III

Expression of P2 By DB117 (pEJH39-1)

In order to further confirm that DB117 (pEJH39-1) actually produces the proper P2 species, a series of confirmatory experiments was performed. One such experiment involved comparing the SDS-polyacrylamide gel profile of the various strains, both coumassie blue stained as well as western blotting using an anti-P2 monoclonal antibody.

FIG. 3 shows the coumassie blue stained SDS-polyacrylamide gel pattern of total cell protein of DL42, DB117, DB117 (pGJB103) and DB117 (pEJH39-1) cells. The gel system used in these experiments is that described by Gulig, et al. (5) except that no B-mercaptoethanol was used. It will be appreciated that both the pathogenic DL42 as well as the DB117 (pEJH39-1) transformed laboratory Hib strain produce a 39K protein (arrow) not found in either untransformed DB117 or pGJB103-transformed DB117 (the faint band at 39K seen in the DB117 is distinct from Hib P2—see FIG. 4).

To confirm the results implied from the coumassie blue pattern, an identical gel was blotted to nitrocellulose and western blot probed generally by the method of Towbin et al. (16). After electrophoretic transfer to nitrocellulose membranes the membrane was reacted with monoclonal antibody 9F5. In contrast to antibody 2F4, this antibody reacts with P2 from both Hib strains and *Haemophilus influenzae* Rd strains.

Figure 4:
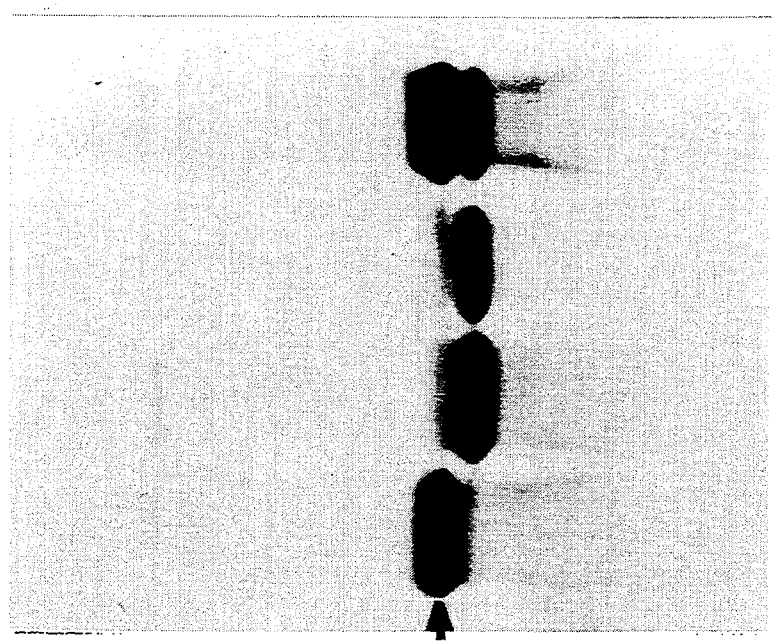

As shown in FIG. 4, this monoclonal antibody recognized only the Hib 39 K P2 species in DL42 (arrow), whereas in both DB117 and DB117 (pGJB103) only the *Haemophilus influenzae* Rd P2 variant at 37 K is recognized. However, in the pEJH39-1-transformed DB117, clearly both varieties of P2 are being produced.

EXAMPLE IV

Preparation of P2 From DL42 (pEJH39-1)

In order to produce a production strain transformant, the Hib strain from which the starting genomic DNA was obtained, DL42, was transformed with the P2 vector pEJH39-1. Briefly, this was accomplished with plasmid pEJH 39-1, using the lactate-glycerol shock transformation method described in the examples above. Transformants were selected on BHIs agar containing tetracycline.

Figure 5:
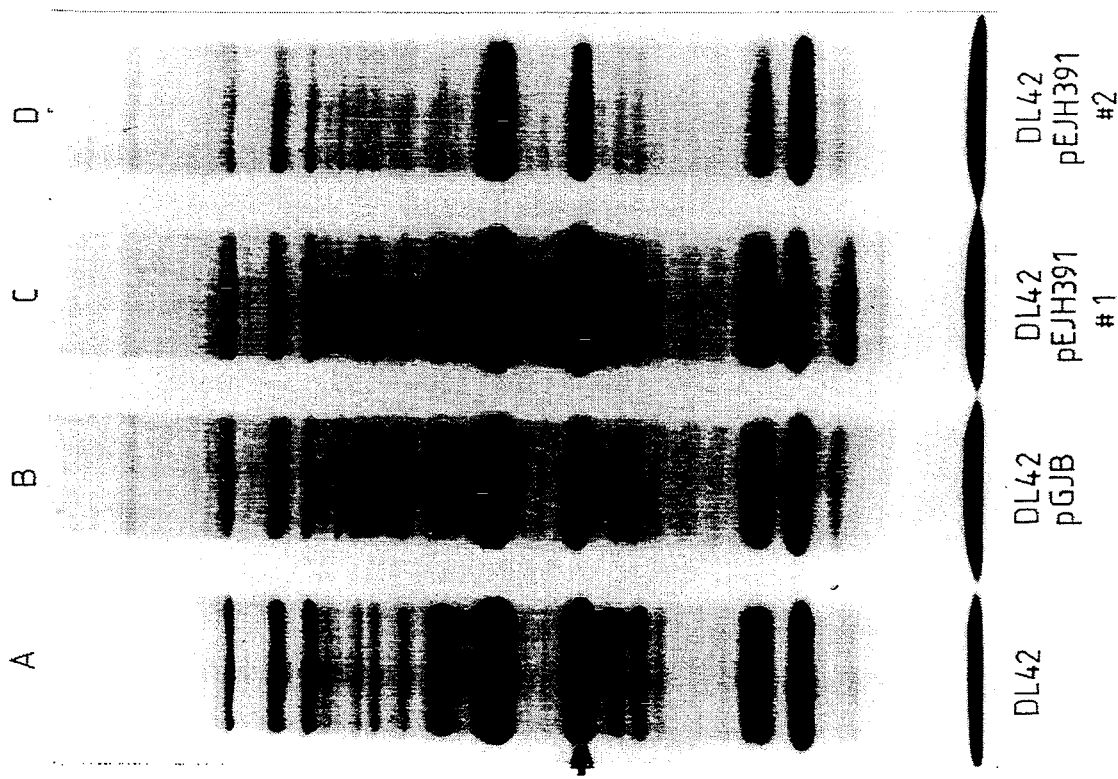

Two different types of transformants were obtained from this experiment as determined by SDS-PAGE coumassie blue staining of total cell proteins. FIG. 5 displays the total cell protein profiles of four strains. The lane labeled DL42 is the wild type host strain. The lane labeled DL42 pGJB is DL42 containing the vector plasmid pGJB103. The lane labeled pEJH39-1 #1 displays a pEJH39-1 transformant which synthesizes significantly more P2 protein than does the wild type DL42 strain. The lane labeled pEJH39-1 #2 contains a transformant that synthesizes no more P2 protein than does the wild-type DL42. It is important to note that the transformant strain DL42 (pEJH 39-1) #1 provides more P2 protein for purification purposes than does the wild type DL42 strain. It is hypothesized that the #1 and #2 transformants represent transformants wherein the recombinant P2 gene has either been chromasomally integrated (#2) or which remains, and is transcribed, extrachromasomal (#1) within the recombinant host cell.

Strain DL42 (pEJH39-1) #1 was deposited with the American Type Culture Collection on Dec. 8, 1987, under the provisions of the Budapest Treaty and accorded accession number 67575.

Protein P2 can be purified from Hib strain DL42 (pEJH 39-1) #1 by the following method. The procedure is modified from that of Munson, et al. (6). Briefly, Hib strain DL42 (pEJH 39-1) #1 cells from 2-4 liters of broth culture are harvested by centrifugation at 10,400×g for 2 min at 4° C. The cell pellets are frozen at −70° C. for at least 18 hrs. Cells are then thawed, suspended in 50 ml of 50 mM N-2-hydroxyethylpiperazine-$N^1$-2-ethanesulfonic acid, pH 7.4 (HEPES buffer).

The cells are disrupted by use of a sonicator (Branson Sonic Power Co., model 350) equipped with a heavy-duty tip operating at maximum power, using 50% duty twice for 5 min with a 5 min interval between sonication periods. The suspension is kept cold by immersion in an ice bath at all times. Unbroken cells are removed by centrifugation at 1900×g for 20 min at 4° C., and the cell envelopes are harvested by centrifugation at 46,000×g for 60 min at 4° C.

Cell envelopes are frozen overnight at −70° C. The following day, the cell envelopes are homogenized in HEPES buffer to a final protein concentration of 10 mg/ml, as determined by Lowry assay. An equal volume of HEPES buffer containing 2% (wt/vol) sodium lauryl sarcosinate is added to the cell envelope homogenate, and the suspension is stirred for 30 min at room temperature ("RT"). The suspension is then centrifuged at 105,000×g for 60 min at 4° C. The outer membrane-enriched pellet is homogenized in 1.5 volumes (relative to the original volume of the cell envelope homogenate) of deoxycholate buffer (50 mM Tris-HCl, pH 8.0, containing 2% (wt/vol) sodium deoxycholate, 0.2 M NaCl, and 5 mM EDTA). The suspension is stirred for 30 min at RT and then centrifuged at 105,000×g for 60 min at RT. The new pellet is homogenized in 10 ml of deoxycholate buffer and centrifuged as before.

The resultant pellet is homogenized in Z3-14 buffer (25 mM imidazole, pH 6.5 containing 0.4% (wt/vol) Zwittergent 3-14) to aprotein concentration of about 2 mg/ml, as determined by the Lowry assay. The suspension is stirred for 30 min at RT, and centrifuged at 105,000×g for 60 min at RT. Triton X-100 is added to the resultant supernatant to a final concentration of 0.5% (vol/vol). The solution is then loaded on a DEAE-Sephacryl column (column volume=1 ml Sephacryl/mg of protein in the sample) which has been pre-equilibrated in Z3-14 buffer containing 0.5% (vol/vol) Triton X-100. After loading, the column is-washed with 50 ml of Z3-14 buffer containing 0.5%.Triton X-100 and 0.05M KCl. The P2 protein is eluted from the column with a linear gradient of 0.05M KCl increasing to 0.4M KCl (volume of gradient=7×column volume).

Fractions of 1.0 ml volume are collected and absorbence at 280 nm is monitored for detection of protein. The protein-containing fractions are pooled, and protein is precipitated by the addition of two volumes of 95% (vol/vol) ethanol followed by storage overnight at—20° C. The resultant precipitate containing the purified 39K protein is collected by centrifugation at 27,000×g for 30 min at 4° C., dried by exposure to a stream of nitrogen resuspended in distilled water, and frozen at—70° C.

The present invention has been described in terms of particular embodiments found or proposed by the present inventor to comprise preferred modes for the practice of the invention. It will be appreciated by those of skill in the art that, in light of the present disclosure, numerous modifications and changes can be made in the particular embodiments exemplified without departing from the intended scope of the invention. For example, due to codon redundancy, changes can be made in the underlying DNA sequence without affecting the protein sequence. Moreover, due to biological functional equivalency considerations, changes can be made in protein structure without affecting in kind or amount of the biological action. All such modifications are intended to be included within the scope of the appended claims.

TABLE II

DNA AND AMINO ACID SEQUENCE OF P2 PROTEIN

| | |
|---|---|
| GACAATTCTA TTGGAGAAAG TTCAATCATA GATAGTAAAC AACCATAAGG AATACAAATT | 60 |
| ATG AAA AAA ACA CTT GCA GCA TTA ATC GTT GGT GCA TTC GCA GCT TCA<br>Met Lys Lys Thr Leu Ala Ala Leu Ile Val Gly Ala Phe Ala Ala Ser<br>1                5                    10                15 | 108 |
| GCA GCA AAC GCA GCT GTT GTT TAT AAC AAC GAA GGG ACT AAC GTA GAA<br>Ala Ala Asn Ala Ala Val Val Tyr Asn Asn Glu Gly Thr Asn Val Glu<br>          20                    25                    30 | 156 |
| TTA GGT GGT CGT TTA AGC ATT ATC GCA GAA CAA AGT AAT AGC ACT GTA<br>Leu Gly Gly Arg Leu Ser Ile Ile Ala Glu Gln Ser Asn Ser Thr Val<br>        35                    40                    45 | 204 |
| GAT AAT CAA AAA CAG CAA CAC GGT GCA TTA CGC AAT CAA GGT TCA CGT<br>Asp Asn Gln Lys Gln Gln His Gly Ala Leu Arg Asn Gln Gly Ser Arg<br>        50                    55                    60 | 252 |
| TTC CAC ATT AAA GCA ACT CAT AAC TTC GGT GAT GGT TTC TAT GCA CAA<br>Phe His Ile Lys Ala Thr His Asn Phe Gly Asp Gly Phe Tyr Ala Gln<br>65                    70                    75                    80 | 300 |

TABLE II-continued
DNA AND AMINO ACID SEQUENCE OF P2 PROTEIN

| | |
|---|---|
| GGT TAT TTA GAA ACT CGT TTT GTT ACA AAA GCC TCT GAA AAC GGT TCA<br>Gly Tyr Leu Glu Thr Arg Phe Val Thr Lys Ala Ser Glu Asn Gly Ser<br>                      85                    90                    95 | 348 |
| GAT AAC TTC GGT GAT ATT ACA AGC AAA TAT GCT TAT GTT ACT TTA GGA<br>Asp Asn Phe Gly Asp Ile Thr Ser Lys Tyr Ala Tyr Val Thr Leu Gly<br>              100                    105                    110 | 396 |
| AAT AAA GCA TTC GGT GAA GTA AAA CTT GGT CGT GCG AAA ACT ATT GCT<br>Asn Lys Ala Phe Gly Glu Val Lys Leu Gly Arg Ala Lys Thr Ile Ala<br>          115                    120                    125 | 444 |
| GAT GGC ATA ACA AGT GCA GAA GAT AAA GAA TAT GGC GTT CTC AAC AAT<br>Asp Gly Ile Thr Ser Ala Glu Asp Lys Glu Tyr Gly Val Leu Asn Asn<br>      130                    135                    140 | 492 |
| AGT GAC TAT ATT CCT ACT AGT GGT AAT ACC GTT GGC TAT ACT TTT AAA<br>Ser Asp Tyr Ile Pro Thr Ser Gly Asn Thr Val Gly Tyr Thr Phe Lys<br>145                    150                    155                    160 | 540 |
| GGT ATT GAT GGT TTA GTA TTA GGC GCT AAT TAT TTA TTA GCA CAA AAG<br>Gly Ile Asp Gly Leu Val Leu Gly Ala Asn Tyr Leu Leu Ala Gln Lys<br>              165                    170                    175 | 588 |
| CGT GAG GGT GCA AAA GGT GAA AAT AAG CGG CCT AAT GAT AAG GCT GGT<br>Arg Glu Gly Ala Lys Gly Glu Asn Lys Arg Pro Asn Asp Lys Alka Gly<br>          180                    185                    190 | 636 |
| GAA GTA CGT ATA GGT GAA ATC AAT AAT GGA ATT CAA GTT GGT GCA AAA<br>Glu Val Arg Ile Gly Glu Ile Asn Asn Gly Ile Gln Val Gly Ala Lys<br>              195                    200                    205 | 684 |
| TAT GAT GCA AAC GAC ATC GTT GCA AAA ATT GCT TAT GGT AGA ACT AAC<br>Tyr Asp Ala Asn Asp Ile Val Ala Lys Ile Ala Tyr Gly Arg Thr Asn<br>      210                    215                    220 | 732 |
| TAC AAA TAT AAC GAA TCT GAC GAG CAT AAA CAG CAA TTA AAT GGT GTA<br>Tyr Lys Tyr Asn Glu Ser Asp Glu His Lys Gln Gln Leu Asn Gly Val<br>225                    230                    235                    240 | 780 |
| TTA GCA ACT TTA GGC TAT CGT TTT AGT GAT TTA GGC TTA TTA GTG TCT<br>Leu Ala Thr Leu Gly Tyr Arg Phe Ser Asp Leu Gly Leu Leu Val Ser<br>              245                    250                    255 | 828 |
| CTA GAT AGT GGC TAT GCA AAA ACT AAA AAC TAT AAA ATT AAA CAC GAA<br>Leu Asp Ser Gly Tyr Ala Lys Thr Lys Asn Tyr Lys Ile Lys His Glu<br>          260                    265                    270 | 876 |
| AAA CGC TAT TTC GTA TCT CCA GGT TTC CAA TAT GAA TTA ATG GAA GAT<br>Lys Arg Tyr Phe Val Ser Pro Gly Phe Gln Tyr Glu Leu Met Glu Asp<br>          275                    280                    285 | 924 |
| ACT AAT GTC TAT GGC AAC TTC AAA TAT GAA CGC ACT TCT GTA GAT CAA<br>Thr Asn Val Tyr Gly Asn Phe Lys Tyr Glu Arg Thr Ser Val Asp Gln<br>      290                    295                    300 | 972 |
| GGT GAA AAA ACA CGT GAA CAA GCA GTA TTA TTC GGT GTA GAT CAT AAA<br>Gly Glu Lys Thr Arg Glu Gln Ala Val Leu Phe Gly Val Asp His Lys<br>305                    310                    315                    320 | 1020 |
| CTT CAC AAA CAA CTA TTA ACC TAT ATT GAA GGT GCT TAC GCT AGA ACT<br>Leu His Lys Gln Leu Leu Thr Tyr Ile Glu Gly Ala Tyr Ala Arg Thr<br>              325                    330                    335 | 1068 |
| AGA ACA ACT GAG ACA GGT AAA GGC GTA AAA ACT GAA AAA GAA AAA TCA<br>Arg Thr Thr Glu Thr Gly Lys Gly Val Lys Thr Glu Lys Glu Lys Ser<br>              340                    345                    350 | 1116 |
| GTG GGT GTA GGT TTA CGC GTT TAC TTC TAA TCAT TTGTTAGAAA TACATTATTA<br>Val Gly Val Gly Leu Arg Val Tyr Phe<br>          355                    360 | 1150 |
| AAAGCAAGGC GAATCGAAAG ATTCCGTTTT TTTGCTCAAA ATCAAGTTAA AAAATGATTA | 1210 |
| AGTTAAAAGT GTATAAATAT TTAGGCTATT TTATAAGTAA CAAAATATTA ATAAAAATCT | 1270 |
| GTGACATATA TACACAGATT T | 1311 |

Based on amino acid sequence analyses of the mature P2 protein, it has been determined that the first 20 amino The references listed below are hereby incorporated by reference.

REFERENCES

1. Tiller, T. L., Jr., and R. H. Buckley, (1978) *J. Pediatrics*, 92:347–353;
2. Gulig, et al., (1982), *Infect, Immun.*, 37:82–88;
3. Shenep, J. L., et al., (1983) *Infect. Immun.*, 42:257–263;
4. Granoff, D. M., et al., (1986) *J. Infect. Dis.*, 153:448–461;
5. Gulig, P. A., et al., (1982) *Infect. Immun.*, 37:82–88;
6. Munson, et al., (1983), *J. Clin. Invest.*, 72:677–684;
7. Vachon, V., et al., (1985) *J. Bacteriol.*, 162:918–924;
8a. Gulig, P. A., and E. J. Hansen (1985) *Infect. Immun.*, 49:819–827;
8. Danner, et al., (1982), *Gene*, 18:101–105.
9. McCarthy, D., et al., (1982), *J. Bacteriol.*, 151:1605–1607;
10. Gulig, P. A., et al., (1983) *Infect Immun.*, 42:516–524;
11. Holmans, et al., (1985), *Infect. Immun.*, 50:236–242;
12. Bricker, J., et al., (1983) *Proc. Nat. Acad. Sci.*, 80:2681–2685;
13. Southern, E. M. (1975), *J. Mol. Biol.*, 98:503–517;
14. Swancutt, M. A., et al., (1986) *Infect. Immun.*, 52:110–119;
15. deGraaff, et al., (1976), *J. Bacteriol.*, 126:439–446:
16. Towbin, et al., (1979), *Proc. Nat. Acad. Sci.*, 76:4350–4354;
17. Stinchcomb, et al., (1979), *Nature*, 282:39;
18. Tschemper, et al., (1980), *Gene*, 10:157;
19. Jones, (1977), *Genetics*, 85:12;
20. Hitzeman, (1980), *J. Biol. Chem.*, 255:12073;
21. Holland, et al., (1978), *Biochemistry*, 17:4900;
22. *Tissue Culture*, Academic Press, Kruse and Patterson, editors (1973);
23. Fiers, et al., (1978), *Nature*, 273:113;
24. Setlow, et al., (1968), *Jrnl. Bacteriol.*, 95:546–558;
25. Lepow, M. L., et al., (1987), *Jrnl. Infect. Dis.*, 156:591–596.
26. Hopp, T. P., and K. R. Woods (1981). Prediction of protein antigenic determinants from amino acid sequences. *Proc. Natl. Acad. Sci. USA*, 78:3824–3828.
27. Kyte, J., and R. F, Doolittle (1982). A simple method for displaying the hydrophatic character of a protein. *J. Mol. Biol.*, 157:105–132.
28. Horn, J. E., T. Quinn, M. Hammer, L. Palmer, and S. Falkow (1986). Use of nucleic acid probes for the detection of sexually transmitted infectious agents. *Diag. Microbiol. Infect. Dis.*, 4:101S–109S.
29. Moseley, S. L., I. Huq, A.R.M.A. Alim, M. So, M. Smadpour-Motalebi, and S. Falkow (1980). Detection of enterotoxigenic *Escherichia coli* by DNA colony hybridization. *J. Infect. Dis.*, 142:892–898.
30. Bryan, R. N., J. L. Ruth, R. D. Smith and J. M. LeBon (1986). Diagnosis of clinical samples with synthetic oligonucleotide hybridization probes, p. 112–116. In L. Leive (ed.), *Microbiology* 1986. American Society for Microbiology, Washington, D.C.
31. Adelman et al., (1983), *DNA* 2:183.
32. Messing et. al., Third Cleveland Symposium on Macromolecules and Recombinant DNA, Editor A. Walton, Elsevier, Amsterdam (1981).
33. Crea et al., (1978), *Proc. Natl. Acad. Sci. U.S.A.*, 75:5765.

What is claimed is:

1. A substantially purified segment of DNA comprising a DNA segment which encodes a *Haemophilus influenzae* P2 antigen.

2. The DNA segment of claim 1 further comprising a control region which allows the expression of the antigen DNA sequence in a recombinant host.

3. The DNA segment of claim 2, further defined as comprising a DNA sequence which encodes a P2 antigen having an amino acid sequence as shown in Table 2.

4. The DNA segment of claim 1 further comprising an origin of replication which allows the replication of the antigen DNA sequence in a recombinant host.

5. The DNA segment of claim 4 wherein said origin comprises a Haemophilus influenzae origin, allowing the replication of the antigen DNA sequence in a *Haemophilus influenzae* host.

6. The DNA segment of claim 1, further defined as a recombinant transformation vector.

7. The DNA segment of claim 1, further defined as comprising a DNA sequence which encodes a P2 antigen having an amino acid sequence as shown in Table 2.

8. The DNA segment of claim 6, wherein the DNA sequence encodes at least an antigenic portion of the amino acid sequence of Table 2.

9. DNA segment of claim 8, wherein the DNA sequence encodes an amino acid sequence extending from the amino acid Ala at position 21 through the amino acid Phe at position 361.

10. The DNA segment of claim 8, wherein the DNA sequence encodes an amino acid sequence extending from the amino acid Gln at position 175 through the amino acid Gly at position 197.

11. The DNA segment of claim 8, wherein the DNA sequence encodes an amino acid sequence extending from the amino acid Gly at position 260 through the amino acid Tyr at position 275.

12. The DNA segment of claim 8, wherein the DNA sequence encodes an amino acid sequence extending from the amino acid Lys at position 296 through the amino acid Gln at position 311.

13. The DNA segment of claim 8, wherein the DNA sequence encodes an amino acid sequence extending from the amino acid Ala at position 333 through the amino acid Val at position 353.

14. A recombinant vector comprising a DNA segment in accordance with anyone of claims 1–2 or 4–13.

15. A nucleic acid molecule at least 17 nucleotides in length, said molecule consisting essentially of an oligonucleotide havinq a sequence which corresponds to at least 17 contiguous nucleotides of the nucleic acid sequence of Table 2.

16. A nucleic acid molecule comprising at least a 17 nucleotide segment of the P2 antigen nucleic acid sequence of Table 2, said molecule being capable of hybridizing to the nucleic acid sequence of Table 2, or the recombinant insert of plasmid pEJH39-1, under hybridization stringency conditions of from 0.02M to 0.15M NaCl at temperatures of from 50° to 70° C.

17. The nucleic acid molecule of claim 16, further defined as comprising at least a 17 nucleotide segment of the nucleic acid sequence of Table 2.

18. A recombinant vector comprising a nucleic acid molecule in accordance with anyone of claims 15–17.

19. A recombinant cell comprising an extrachromosomal DNA segment encoding a *Haemophilus influenzae* P2 antigen 20. The recombinant cell of claim 19, further defined as a recombinant *Haemophilus influenzae* cell.

21. A method for preparing transformed *Haemophilus influenzae* cells useful in the production of *Haemophilus influenzae* P2 antigen comprising:
  (a) transforming *Haemophilus influenzae* host cells with a recombinant vector which includes a DNA sequence encoding a *Haemophilus influenzae* P2 antigen; and
  (b) selecting transformants which express the antigen encoded by the DNA sequence.

22. The method of claim 21 wherein said *Haemophilus influenzae* host cells comprise cells which produce the *Haemophilus influenzae* P2 antigen.

23. A method for preparing *Haemophilus influenzae* P2 antigen comprising preparing a *Haemophilus influenzae* transformant in accordance with claim 21 or 22, culturing said transformants in a manner effective to obtain expression of said antigen; and preparing said antigen therefrom.

24. A method for preparing an immunogen composition comprising preparing *Haemophilus influenzae* P2 antigen in accordance with claim 23 and admixing said antigen with a pharmaceutically acceptable diluent or adjuvant.

25. A *Haemophilus influenzae* transformant, prepared by the process of claim 21 or 22.

26. A method for preparing recombinant cells useful in the production of *Haemophilus influenzae* P2 antigen comprising:
  (a) transforming host cells with a recombinant vector which includes a DNA sequence encoding a *Haemophilus influenzae* P2 antigen; and
  (b) selecting transformants which express the antigen encoded by the DNA sequence.

* * * * *